(12) United States Patent
Nesbitt

(10) Patent No.: US 7,093,595 B2
(45) Date of Patent: Aug. 22, 2006

(54) PORTABLE MEDICATION INHALATION KIT

(75) Inventor: Robert Richardson Nesbitt, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/489,490

(22) PCT Filed: Oct. 2, 2002

(86) PCT No.: PCT/US02/29829

§ 371 (c)(1),
(2), (4) Date: Mar. 12, 2004

(87) PCT Pub. No.: WO03/030974

PCT Pub. Date: Apr. 17, 2003

(65) Prior Publication Data

US 2005/0172961 A1    Aug. 11, 2005

Related U.S. Application Data

(60) Provisional application No. 60/327,761, filed on Oct. 8, 2001.

(51) Int. Cl.
*A61M 15/00* (2006.01)

(52) U.S. Cl. .................. 128/203.15; 206/363; 206/438

(58) Field of Classification Search ........... 128/203.15, 128/203.21, 203.18, 203.12; 206/532, 828, 206/530, 534, 363, 438; 221/25; D24/110
See application file for complete search history.

(56) References Cited

U.S. PATENT DOCUMENTS

| | | | |
|---|---|---|---|
| 4,660,991 A | 4/1987 | Simon | |
| D377,861 S | 2/1997 | Jacober | |
| 5,779,122 A | 7/1998 | Martinelli | |
| 5,830,490 A | 11/1998 | Weinstein et al. | |
| 5,833,066 A | 11/1998 | Hargus et al. | |
| 6,056,118 A | 5/2000 | Hargus et al. | |
| 6,082,544 A * | 7/2000 | Romick | 206/531 |
| 6,447,751 B1 | 9/2002 | Weinstein et al. | |
| 6,540,082 B1 * | 4/2003 | Peterson | 206/534 |
| 6,637,431 B1 * | 10/2003 | Ekelius et al. | 128/203.15 |

FOREIGN PATENT DOCUMENTS

| | | |
|---|---|---|
| AU | 695183 | 2/1997 |
| WO | WO 01/45777 A1 | 6/2001 |

* cited by examiner

Primary Examiner—Henry Bennett
Assistant Examiner—Shumaya B. Ali
(74) Attorney, Agent, or Firm—Edward J. Prein (57) ABSTRACT

A portable kit (20) in which is conveniently retained the materials required for a user to pulmonarily delivery inhaleable medication. The kit (20) includes a carrying case (22) in which a plurality of individual doses (5) of an inhaleable medication are removably mounted. An inhaler (40) is also mountable in the case (22), and when removed from the case (22) is operable to pulmonarily administer one of the medication doses (57) loaded by a user into the inhaler (40). A dosing guidance system (70) is also provided within the case (22) in registry with the plurality of individual doses (57) of medication, which dosing guidance system (70) provides a quick, visual reminder to assist the user in taking doses as prescribed by her physician.

14 Claims, 5 Drawing Sheets

PORTABLE MEDICATION INHALATION KIT

This is the national phase application, under 35 USC 371, for PCT/US02/29829, filed Oct. 2, 2002, which claims the benefit, under 35 USC 119(e), of U.S. Provisional Application 60/327,761, filed Oct. 8, 2001.

BACKGROUND OF THE INVENTION

The present invention pertains to portable kits used to administer medicine, and, in particular, to a portable kit including an inhaler for pulmonary administration of medicine.

In order to manage a variety of medical conditions, such as diabetes, patients often must self-administer their medication. For patients leading active lives, these medications frequently must be carried around by a patient for administration on the go and without the direct supervision of a health care professional.

The use of an assortment of different types of inhalers or inhalation devices is known to pulmonarily deliver inhaleable medications. To allow a user to conveniently carry around an inhaler, various cases have been developed. One such carrying case is disclosed in U.S. Pat. No. 5,833,066. The case includes a counter mechanism manually operable by the user to keep track of the number of doses dispensed from the inhaler storable in the case, such as a metered-dose inhaler. While the manual counter mechanism may be beneficial with a metered-dose inhaler, in which a canister with a large supply of doses is initially loaded, in that it helps a user gauge when that large supply is nearing exhaustion, the counter mechanism offers little if any reminder as to when the last dose was taken, and further the case does not organize additional medicine to be administered by the inhaler in such a way as to serve as such a reminder or indicator of the last taken dose.

One known portable kit for parenteral administration of insulin employs a reusable injection pen which can be stored when not in use within a complementarily shaped internal hollow provided in a clamshell type case. The interior of the case also provides separate hollows adapted to accommodate replacement needles for the pen, as well as a replacement cartridge, which cartridge holds multiple doses of medicine and is loadable into the pen when the medicine in the replaceable cartridge already loaded in the pen is exhausted. While useful for treating diabetes, this kit is not useful for pulmonary delivery of medicine, nor does visually observing the way the replacement cartridge is arranged in the case offer any indication of when the previous dose may have been administered.

Other carrying cases have been developed to hold packages of medicines, such as child-resistant containers intended to be loaded with blister packs. Furthermore, known ways of packaging medicine include providing instructions on the medicine's packaging and associated with blister packaged doses of that packaging. Alternate modes include removable labels on the packaging and associated with blister packaged doses of that packaging which can be applied to a calendar to remind a user to administer a dose. However, if used with a system for inhaleable medicine delivery requiring administration via an inhaler, the combination of case and packaging designs may require a user to separately keep track of the inhaler, which, if it becomes separated from the medicine, can be at minimum, inconvenient, and at worst, hinder appropriate compliance.

Thus, it would be desirable to provide a system that overcomes at least one of these and other shortcomings of the prior art.

BRIEF SUMMARY OF THE INVENTION

In one form thereof, the present invention provides a portable medication inhalation kit including a carrying case, a plurality of individual doses of a dry powder medication removably mountable on a first surface portion of the carrying case, means for guiding dosing on a second surface portion of the carrying case in registry with the plurality of individual doses of dry powder medication, and a dry powder inhaler removably mountable on a third surface portion of the carrying case, which inhaler, when removed from the carrying case, is operable to pulmonarily administer one of the plurality of individual doses of dry powder medication loaded by a user into the inhaler.

In another form thereof, the present invention provides a carrier for a plurality of individual doses of inhaleable medication and an inhaler operable to pulmonarily administer one of the plurality of individual doses of inhaleable medication loaded by a user into the inhaler. The carrier includes a first part having an exterior surface and an interior surface, and a second part having an exterior surface and an interior surface. The second part is hingedly connected to the first part and pivotable relative thereto between a carrier opening position and a carrier closing position, wherein when in the carrier closing position the first and second parts define an internal volume in which the interior surface of the first part faces the interior surface of the second part. The carrier also includes means on the first part interior surface for removably mounting the plurality of individual doses of inhaleable medication, means on the first part interior surface for guiding dosing of individual doses of inhaleable medicine, and means on one of the first part interior surface and the second part interior surface for removably mounting the inhaler.

One advantage of the present invention is that a portable medication inhalation kit is provided which allows a patient to conveniently, and in an organized fashion, tote around the materials needed to pulmonarily self-administer an inhaleable medication.

Another advantage of the present invention is that a portable medication inhalation kit is provided having an uncomplicated and cost-effective design which is easy and intuitive to use.

Still another advantage of the inventive portable medication inhalation kit is that it allows a user to note personalized instructions for a given dose of medication.

Yet another advantage of the inventive portable medication inhalation kit is that the medicine is stored in a highly visible arrangement to serve as a dosing reminder to the user which allows a user to readily determine whether a given dose has been taken, which may assist a user in complying with the therapy prescribed by a treating physician.

BRIEF DESCRIPTION OF THE DRAWINGS

The above-mentioned and other advantages and objects of this invention, and the manner of attaining them, will become more apparent, and the invention itself will be better understood by reference to the following description of embodiments of the invention taking in conjunction with the accompanying drawings, wherein.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION OF THE INVENTION

Figure 1:
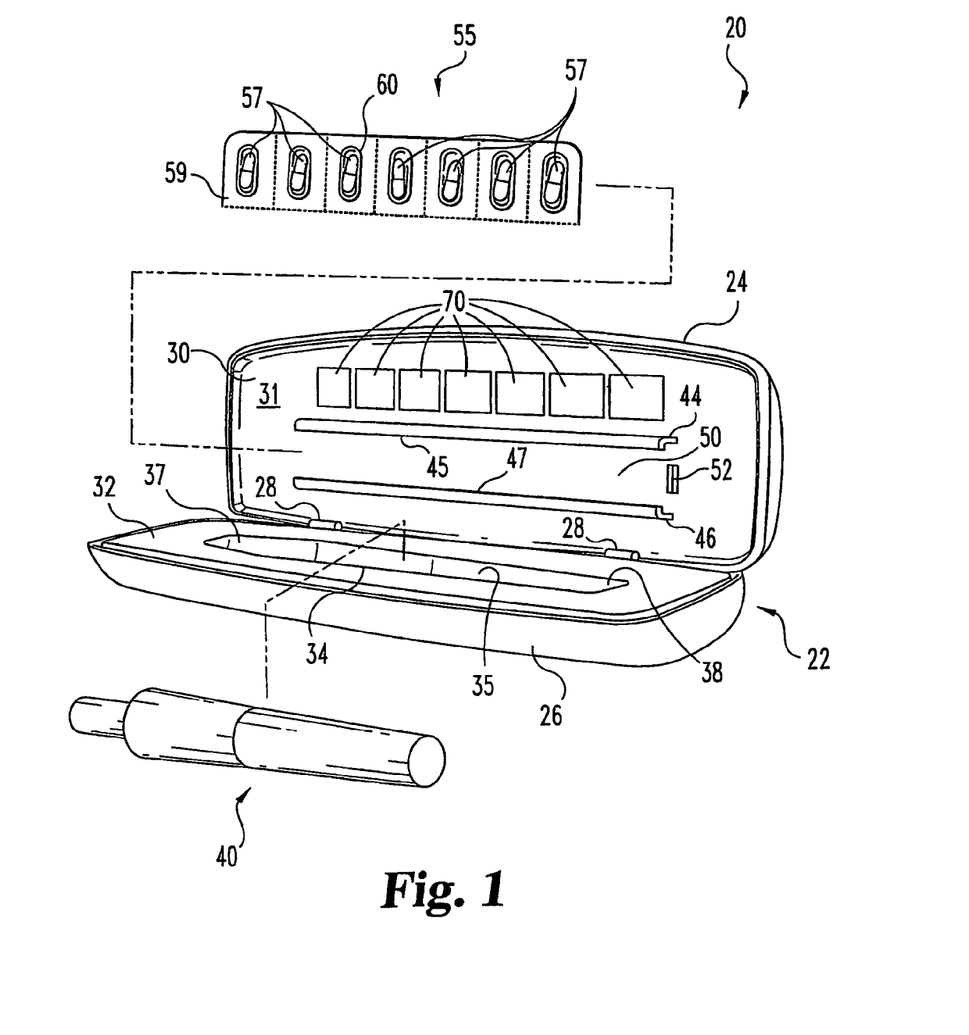
FIG. 1 is a diagrammatic, exploded perspective view of a first embodiment of a portable medication inhalation kit of the present invention.
Figure 2:
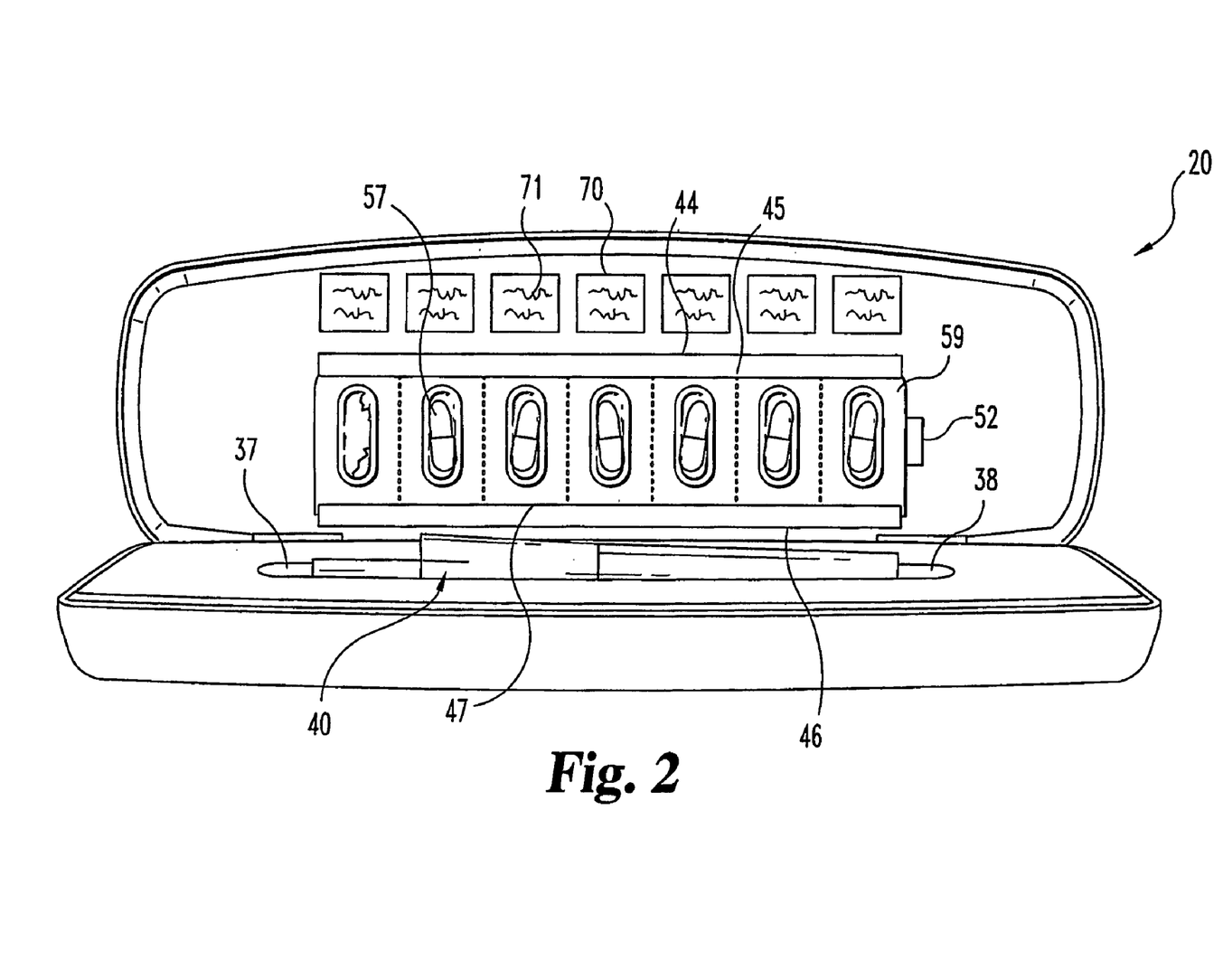
FIG. 2 is a front view of the portable medication inhalation kit of FIG. 1 after the kit has been fully reassembled after an initial use.
Figure 3:
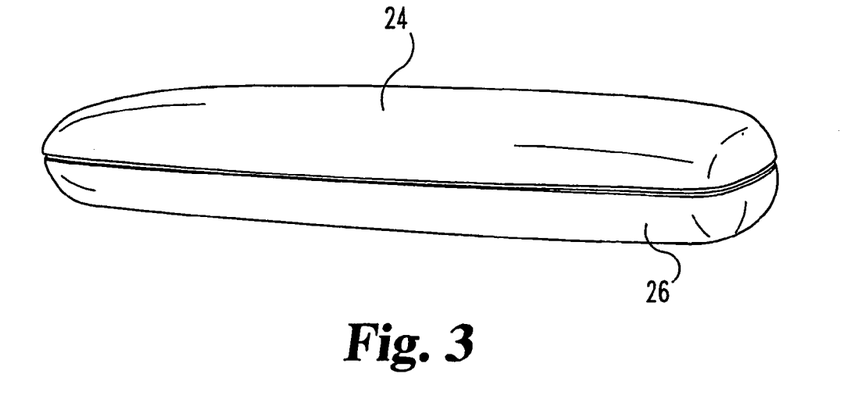
FIG. 3 is a front perspective view of the portable medication inhalation kit of FIG. 1 after being closed from the open arrangement shown in FIG. 1.

Referring now to FIGS. 1, 2 and 3, there is shown an exemplary embodiment of a portable medication inhalation kit of the present invention. The kit, generally designated 20, includes a carrying case 22 which when in the closed arrangement shown in FIG. 3 protectively houses other elements of the kit. In the shown embodiment, case 22 has a clamshell type design similar to common types of eyeglasses cases, but other case designs may naturally be employed. Case 22 has a contoured parallelepiped external shape formed by a top shell or lid 24 and a mating bottom shell or base 26, each made of a durable, rigid material such as plastic. Hinges indicated at 28 connect top shell 22 and bottom shell 26 such that top shell 22 can be pivoted relative to bottom shell 26 from the arrangement shown in FIGS. 1 and 2 to the arrangement shown in FIG. 3 to close the opened case. Hinges 28 may be spring loaded to resist the shell halves when closed together from being opened, and to urge the shell halves to come together unless the case is fully or at least substantially opened. Alternatively, a not shown latching mechanism between the shell halves may be added to prevent inadvertent opening of the carrying case.

The interior surfaces of case 22 are formed of inserts 30 and 32 molded from, for example, a lightweight plastic material. Case inserts 30 and 32 are fixedly attached, such as via snap fits, press fits, or another suitable manner, within top shell 24 and bottom shell 26, respectively.

The central surface region 34 of insert 32 is recessed to define an inhaler accommodating hollow 35. An inhaler, generally shown at 40 and in its capped state in FIG. 1, is insertable within hollow 35. Hollow 35 is sized and shaped to uniquely accommodate the inhaler 40, such that the inhaler is retained securely enough to hold the inhaler in place, even in the event the case is inverted. For example, this could be a "friction-fit". Such an engagement configuration does not require that the depth of hollow 35 accommodate the entire inhaler, but rather, for the tapered cylindrical shape of the inhaler shown, merely slightly more than half of the inhaler diameter being fittable within the hollow may be sufficient. Recessed regions 37 and 38 at either end of hollow 35 permit fingertip gripping of the ends of inhaler 40 to facilitate its being pulled from case insert 32.

In alternate embodiments, rather than a direct frictional engagement with the insert, the inhaler may be mounted to insert 32 using additional fastener elements known in the art, such as straps, clips or hinged levers to hold the inhaler in place, which hinged levers automatically snap over the inhaler when inserted between the levers. Still further, inhaler 40 can be mounted within a shallow hollow in which it is not frictionally retained, but which hollow, in combination with inhaler 40, while still at least partially within the hollow, abutting the underside of the lid when the case is closed but inverted, preventing unrestricted movement of the inhaler within the closed case.

Inhaler 40, when not being stored within carrying case 22, is operable to delivery a dry powder medication into a user in a known fashion. The shown inhaler 40 is of the general type in which a user loads into the inhaler a capsule filled with a single dose of medication, punctures that loaded capsule by mechanical action of the inhaler, and then holds the inhaler to her mouth and inhales the medication which escapes from the punctured capsule, which inhaler type is shown in more detail in U.S. Pat. No. 4,995,385 entitled "Inhaler With Regular Complete Emptying Of The Capsule," the entire disclosure of which is incorporated herein by reference. The inhaler description herein is illustrative and not intended to be limiting, however, as the design of the inhaler, other than its ability to be stored in the carrying case and usable to deliver doses of medication that were stored in that same case, is not material to the present invention, and other types of inhalers may be substituted for inhaler 40 within the scope of the invention.

Preferably on case insert 30 as shown, but alternatively on case insert 32, retainers are provided to removable mount a supply of individual doses of medicine within case 22. With reference to FIG. 1, the preferred retainers include a first rail 44 and a second rail 46 which are integrally molded with and project down from the interior facing surface 31 of case insert 30. Rails 44 and 46 are parallel and include facing lip portions 45 and 47 that jut toward each other in spaced apart relationship with insert surface 31. The lipped rails define a slot 50 in which fits a multiple dose medicine pack, generally designated 55. The lipped rails are dimensioned such that the width of pack 55 is less than the space between rails 44 and 46, and greater than the space between lip portions 45 and 47, such that when pack 55 is inserted lengthwise within slot 50 as shown in FIG. 2, the engagement of the pack 55 by the underside of lip portions 45 and 47 prevents the pack from falling down when case 22 is closed.

Although the retaining rails are shown as continuous in the preferred embodiment, discontinuous rails or spaced hooks may be employed in alternate embodiments. Still further, other known retainers, including clips, may be used to hold the medicine pack within the case.

Medicine pack 55 is slidably inserted within slot 50 by being passed between, from the perspective of a FIG. 1 viewer, the left end portions of rails 44 and 46, and under lip portions 45 and 47. Sliding insertion of pack 55 is halted when the inserted pack end abuts a protruding stop 52 formed in case insert surface 31. Rather than as a separate protuberance, a stop member may be formed as a connecting span of rail between rails 44 and 46. Medicine pack 55 after its insertion abutting stop member 52 is shown in FIG. 2.

Medicine pack 55 holds a plurality of individual doses 57 of a medication suitable for delivery by inhaler 40. The term individual doses herein refers to the fact that each dose is separately loaded and then used in inhaler 40. Depending on the needs of a given user, to administer the proper amount of medicine at a given time, more than one of the doses may have to be used by repeated operation of the inhaler. Doses 57 are preferably capsules filled with medicine in a dry powder form. Although blister-packed capsules are shown and are a preferred form of providing medication to the inhaler, capsule-free systems which are loadable into an inhaler may be employed in alternate embodiments.

For example, a foil-pouch system, in which the inhaleable dry powder is merely captured within a puncturable foil pouch, may be employed in an alternate embodiment.

Medicine pack 55 is preferably a blister pack as is known in the art. For example, blister pack 55 includes a relatively rigid base 59, such as made of a transparent, moisture-resistant material such as cellophane, with cavity-defining blisters 60 which are each filled with an individual dose 57. Capsule filled cavities 60 are sealed by a more readily puncturable material 62, such as an aluminized foil, that faces case insert 30 when the pack 55 is installed. Pack 55 is an elongated strip in shape and in which capsules 57 are arranged in a single row.

Figure 4:
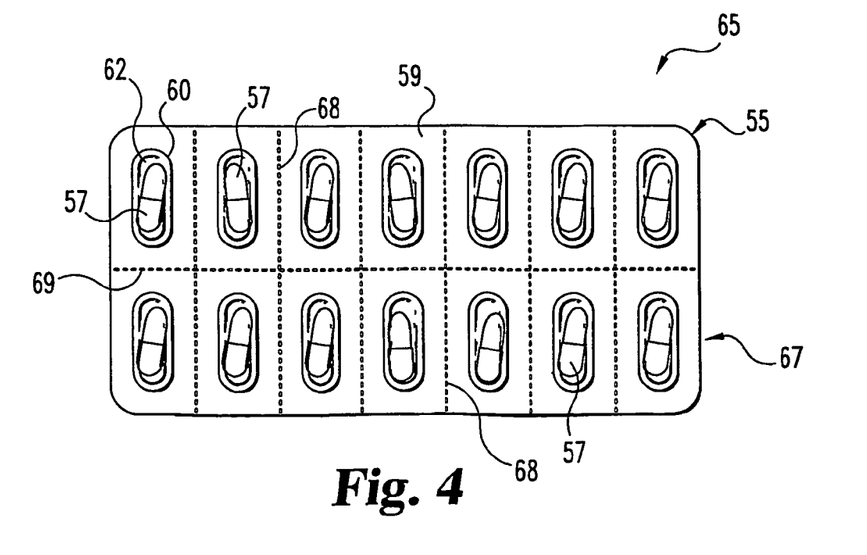
FIG. 4 is front view of one form of medication pack from which can be detached a strip of doses usable as part of the inhalation kit of FIG. 1.

With reference to FIG. 4, medicine pack 55 is taken from a larger blister pack, generally designated 65. Pack 65 includes both strip pack 55 and a second strip pack 67, and even additional strips may be provided. Strip packs 55 and 67 are divided by scoring 69, arranged horizontally in FIG. 4, to allow a user to more easily separate the strip packs. Although each pack is shown including seven doses, such as if the strip pack held a one week supply of one-a-day doses, the number of doses within the strip may be varied by the manufacture. In addition, scoring 68 arranged vertically in FIG. 4 and between each column of capsules 57 permits each strip pack to be divided if the user so desires. Medicine pack 65 may hold capsules all filled with the same type/quantity of medicine. Alternatively, pack 65 may hold capsules filled with different types or quantities of medicine. For example, strip pack 55 may include capsules each filled with five milligrams of inhaleable insulin, while strip pack 67 includes capsules each filled with eight milligrams of inhaleable insulin. Still further, strip pack 55 may include capsules filled with insulin, and strip pack 67 includes capsules filled with daily doses of another therapeutic.

Although the medication being inhaled is further described below as being insulin, the present invention may be used with different types of dry powder medications, for example, human growth hormone and parathyroid hormone.

A system for guiding dosing is housed within case 22 adjacent the dose retaining system. In FIGS. 1 and 2, a series of markable elements 70 are mounted to case insert 30. Markable elements 70 are arranged in a row above rails 44 and 46, and in registry with capsules 57 such that each markable element 70 corresponds to and is located directly above one of the strip pack capsules. Markable elements 70 are preferably dry erase boards, which boards, rather than being attached to case insert 30, may in an alternate embodiment be integrally formed as part of the case insert. A marker which writes on boards 70 with ink that is erasable therefrom is not shown, and further, to allow marking wherever the kit 20 is carried, could be stored within case 22 in another conforming hollow that is not shown.

Seven markable elements 70 spaced at even intervals are shown, which number and spacing corresponds to the seven capsules 57 within pack 55. Different numbers of separated elements 70 may be provided by the manufacturer in alternate embodiments, which number need not be the same as in the packs as long as capsules can still be lined up under the markable elements 70. Still further, a single rectangular markable element, preferably segmented with vertical lines to distinguish between board regions under which are aligned the capsules, may be substituted for the shown multiple spaced apart boards.

Rather than the dry erase boards, other markable materials may be employed as elements 70 within the scope of the present invention. For example, small tablets or pads of disposable paper may be attached to case insert 30, such as with adhesives of with the rigid base panels of the pads inserting within slots in the insert. For such paper pads, when markings on the top sheet of a given pad are no longer applicable, that top sheet is ripped off to expose a clean sheet upon which new markings may be made with, for example, a pen or pencil. Still further, the markable elements may be provided on a disposable insert which slidably inserts between not shown rails similar to, but located above, rails 44 and 46. Although less customizable, indicia such as numbers or letters, or combinations thereof, could be permanently provided on the case insert in still another embodiment to allow a patient to relate a given capsule to information conveyed by the indicia.

Figure 5:
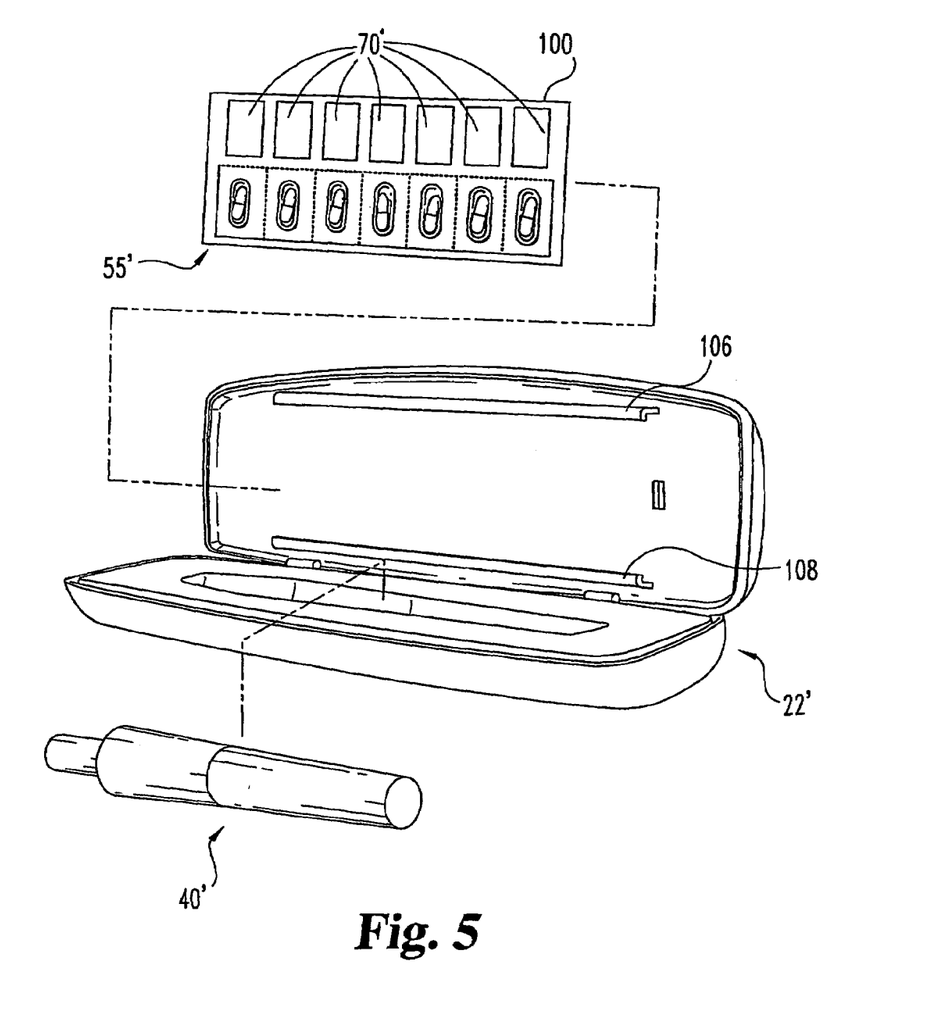
FIG. 5 is a diagrammatic, exploded perspective view of a second embodiment of a portable medication inhalation kit of the present invention.
Figure 6:
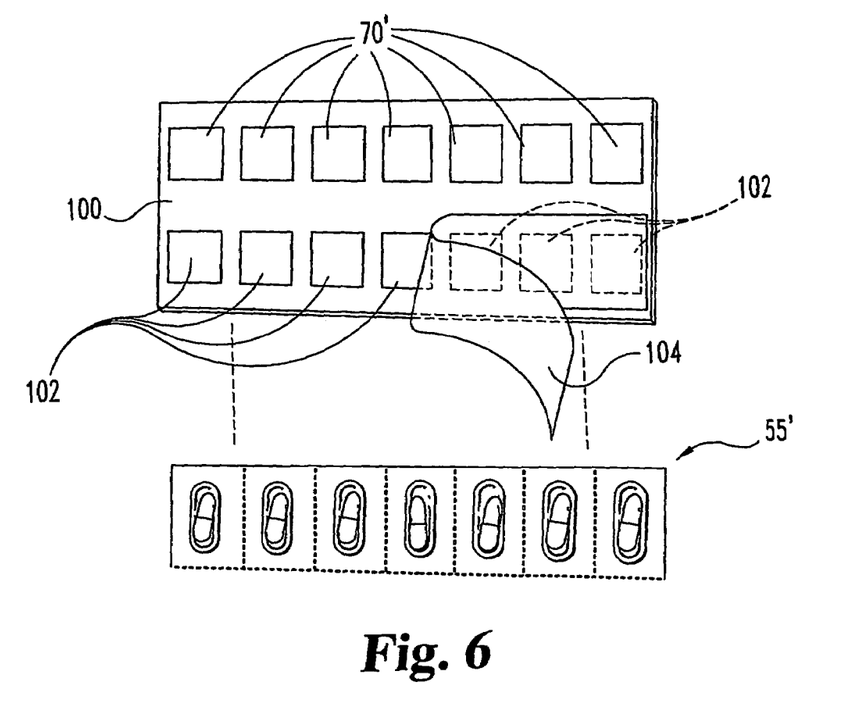
FIG. 6 is a front view of an insert to which is shown being attached a strip of doses usable as part of the inhalation kit of FIG. 5.

Referring now to FIGS. 5 and 6, there is shown an alternate embodiment of a portable medication inhalation kit of the present invention. This kit is similar in many respects to kit 20 of FIGS. 1–4, and selected corresponding parts are therefore indicated with a prime notation. The kit of FIGS. 5–6 differs from kit 20 in that the inhaleable doses are removably mountable on the case via an insert 100. Insert 100 is made of a generally rigid material, such as cardboard, in order to retain its overall shape. At least one adhesive element, and preferably a series of adhesive squares 102 are arranged in a row along the cardboard insert 100 and are covered by a removable, or peel-off, release strip 104. Release strip 104 is initially provided on insert 100, and when the appropriate medication is to be mounted to insert 100, a user first peels off strip 104 and then adheres the medication to the backing strip. The adhesive is of the type which holds the medication securely while allowing the medication to be removed therefrom to be punched out from its packaging and subsequently inserted into the inhaler. In the preferred embodiment, insert 100 further includes markable elements 70' in registry with adhesive elements 102, which elements 70' may be outlined sections of the cardboard insert on which a user makes notations. Insert 100 is sized to slidably fit and be held between rails 106 and 108, which are similar to the rails 44 and 46 of kit 20, but which rails are spaced farther apart than the rails of kit 20 to accommodate insert 100, which is taller than the height of the medication package attached thereto.

The kit of FIGS. 5 and 6 allows additional flexibility in using the kit to inhale different medications, as for example a dose of one strength can be placed at one of the adhesive elements 102, while the adjacent element 102 is provided with a different strength dose. Further, each of these individual doses can be provided with personalized information which is noted on the markable element in registry with that dose.

The structure of portable medication inhalation kit 20 will be further understood in view of the following explanation of its operation. With the kit in the arrangement shown in FIG. 1, which is the configuration in which the kit normally will be received initially but for the fact that the inhaler will typically be installed within a closed case 22, the case is loaded with medication doses to be administered at appropriate times in the future. In particular, strip pack 55, which has been severed along scoring 69 from the remainder of medicine pack 65, is slidably inserted within slot 50 until the inserted end of strip pack 55 abuts stop 52. Then, and depending on the type of markable elements 70 provided, using as appropriate either a dry erase marker or another type of writing instrument, information about the loaded medication can be written on markable element 70. The information can be completed by the user, or by a health care professional overseeing the treatment of the user. The written information, which is represented at 71 in FIG. 2, can include dosing instructions related to which day of the week and/or time of day the particular medication dose in registry below that given instruction needs to be administered, or other data helpful to the user, such as a reminder as to the type of medication being taken. After case 22 is closed, kit 20 can then be carried around conveniently by a patient until medicine is required.

When the time comes to take the medicine, case lid 24 is pivoted up from case base 26. Without removing pack 55 from its mounting, due to the transparent aspect of the blister packaging, the user can quickly ascertain or be reminded of her treatment status by visually observing which, if any, pack blisters have previously been opened, and the notation 71 for the next dose in the row to be administered. Typically the order of doses will start with the leftmost dose from the perspective of a FIG. 2 viewer and proceed to the right. The user then slides blister pack 55 out from between rails 44 and 46, and then in a standard fashion punches the left-most available capsule 57 from the pack through the foil seal, then loads the punched out dose into inhaler 40 which has been removed from the case 22 and uncapped, and operates the inhaler to administer that dose pulmonarily. After the user fully reinserts blister pack 55 between rails 44 and 47, and then removes from the inhaler the spent capsule which is discarded, the user finally caps and replaces inhaler 40 within hollow 35, and assuming the dose just administered was the first dose of pack 55, portable medication inhalation kit 20 is at that moment configured as shown in FIG. 2. Case 22 can then be closed and the kit 20 carried around until needed again. Kit 20 can be used until all the medication doses 57 have been exhausted, at which time the spent strip pack is removed and discarded and a new strip pack can be directly mounted by being inserted between rails 44 and 46. After wiping clean dry erase boards 70 as appropriate, new or modified information 71 can then be written on the dry erase boards 70 for the next set of administrations.

In an alternate embodiment not shown, rather than a single pair of blister pack retaining rails 44 and 46 as is shown in the Figures, and provided case 22 is made sufficiently large, a second set of blister pack retaining rails is provided directly below rails 44 and 46. The second set of rails retains a second strip pack of capsules, which capsules are lined up directly below the capsules retained by rails 44 and 46, to increase flexibility in dosing using a finite number of different medication capsule strengths. For example, assuming capsule strengths of either five milligrams or eight milligrams as in the example above, if a user needs to administer ten milligrams of insulin at one time, separate strip packs, each with five milligrams of insulin per capsule, can be loaded within the sets of rails, and inhaler 40 would be operated twice, a first time with the capsule from the top strip pack, and a second time with the capsule from the bottom strip pack and directly below the first capsule just administered, to deliver the proper dose. Alternatively, a thirteen milligrams insulin dosage can be administered utilizing one strip pack containing capsules with five milligrams of insulin per capsule and a second strip pack with eight milligrams of insulin per capsule.

While this invention has been shown and described as having preferred designs, the present invention may be modified within the spirit and scope of this disclosure. This application is therefore intended to cover any variations, uses or adaptations of the invention using its general principles. Further, this application is intended to cover such departures from the present disclosure as come within known or customary practice in the art to which this invention pertains.

I claim:

1. A portable medication inhalation kit comprising:
   a carrying case including a first surface portion, a second surface portion and a third surface portion;
   a plurality of individual doses of a dry powder medication removably mountable on said case first surface portion;
   means for guiding dosing on said case second surface portion in registry with said plurality of individual doses of dry powder medication, said guiding means including at least one markable element upon which a user may write information such as time of administration, wherein the registry of said at least one markable element with the individual doses includes each one of the individual doses being aligned with either a corresponding one of spaced markable elements of said at least one markable element, or a corresponding segment of said at least one markable element; and
   a dry powder inhaler removably mountable on said case third surface portion, said inhaler, when removed from said carrying case, being operable to pulmonarily administer one of said plurality of individual doses of dry powder medication loaded by a user into said inhaler;
   wherein said plurality of individual doses of a dry powder medication are arranged in a row and individually sealed within a blister pack; and
   wherein said case first surface portion defines a slot for slidably receiving said blister pack, said case first surface portion adapted to retain said blister pack when said blister pack is received in said slot, whereby said doses are aligned with said means for guiding dosing, wherein said carrying case comprises a first surface portion and said second surface portion being regions of an interior surface of said first part, said third surface portion being a region of an interior surface of a second part.

2. The portable medication inhalation kit of claim 1 wherein said plurality of individual doses of a dry powder medication comprises medication filled capsules.

3. The portable medication inhalation kit of claim 1 wherein said first surface portion comprises a pair of rails with facing lips to retain said blister pack.

4. The portable medication inhalation kit of claim 1 wherein said means for guiding dosing comprises at least one dry erase markable surface fixedly secured to or integrated into said case second surface portion.

5. The portable medication inhalation kit of claim 1 wherein said means for guiding dosing comprises at least one replaceable writing tablet removably mountable on said case second surface portion.

6. The portable medication inhalation kit of claim 1 wherein said means for guiding dosing comprises indicia provided directly on said case second surface portion.

7. The portable medication inhalation kit of claim 1 further comprising an insert removably mountable on said case first surface portion and said case second surface portion, said insert including said means for guiding dosing and at least one adhesive element on which said plurality of individual doses of dry powder medication is removably mountable.

8. The portable medication inhalation kit of claim 7 wherein said case first surface portion and said case second surface portion together define a slot for slidably receiving said insert, said case first surface portion and said case second surface portion adapted to retain said insert when said insert is received in said slot.

9. The portable medication inhalation kit of claim 7 wherein said insert comprises a cardboard construction, and further comprising a release strip covering said at least one adhesive element and removable to permit mounting of said plurality of individual doses of dry powder medication.

10. The portable medication inhalation kit of claim 1 wherein said case third surface portion defines a recess in which at least partially insertably fits said inhaler.

11. A carrier for a plurality of individual doses of inhaleable medication and an inhaler operable to pulmonarily administer one of the plurality of individual doses of inhaleable medication loaded by a user into the inhaler, the carrier comprising:
 a first part having an exterior surface and an interior surface;
 a second part having an exterior surface and an interior surface, said second part hingedly connected to said first part and pivotable relative thereto between a carrier opening position and a carrier closing position, wherein when in said carrier closing position said first part and said second part define an internal volume in which said interior surface of said first part faces said interior surface of said second part;
 means on said first part interior surface for removably mounting the plurality of individual doses of inhaleable medication;
 means on said first part interior surface for guiding dosing of individual doses of inhaleable medicine;
 means on one of said first part interior surface and said second part interior surface for removably mounting the inhaler;
 wherein said means for removably mounting the plurality of individual doses of inhaleable medication comprises an insert with at least one adhesive element on which said plurality of individual doses are removably mountable; and
 wherein said means for guiding dosing comprises at least one markable surface on said insert;
 wherein said means for removably mounting the medication comprises a plurality of lipped projections that retain a pack containing a row of medication inserted therebetween; and
 wherein said plurality of lipped projections comprises a pair of parallel rails between which the pack is slidably insertable, wherein said carrying case comprises a first surface portion and said second surface portion being regions of an interior surface of said fist part, said third surface portion being a region of an interior surface of said second part.

12. The carrier of claim 11 wherein said means for removably mounting the inhaler comprises a recess of said second part interior surface in which at least partially insertably fits the inhaler.

13. The carrier of claim 11 wherein said means for guiding dosing comprises at least one dry erase markable surface.

14. The carrier of claim 11 wherein said means for guiding dosing comprises at least one replaceable writing tablet.

* * * * *